United States Patent
Johnson et al.

(10) Patent No.: US 9,799,155 B2
(45) Date of Patent: Oct. 24, 2017

(54) TRACKING AND ACCESS SYSTEM

(71) Applicant: Bohnas LLC, Henderson, NV (US)

(72) Inventors: Casey Johnson, Coeur d'Alene, ID (US); Greg Bauer, Post Falls, ID (US); Doran Thomas, Post Falls, ID (US)

(73) Assignee: Bohnas LLC, Henderson, NV (US)

( * ) Notice: Subject to any disclaimer, the term of this patent is extended or adjusted under 35 U.S.C. 154(b) by 6 days.

(21) Appl. No.: 14/947,832

(22) Filed: Nov. 20, 2015

(65) Prior Publication Data

US 2017/0148239 A1   May 25, 2017

(51) Int. Cl.
G06F 7/00    (2006.01)
G07C 9/00    (2006.01)

(52) U.S. Cl.
CPC ............... *G07C 9/00111* (2013.01)

(58) Field of Classification Search
CPC .................. G05D 7/0635; G07C 9/00111
USPC .......................................... 340/5.7
See application file for complete search history.

(56) References Cited

U.S. PATENT DOCUMENTS

| | | | |
|---|---|---|---|
| 4,804,945 A | 2/1989 | Millet | |
| 5,918,596 A | 7/1999 | Heinonen | |
| 6,658,322 B1 | 12/2003 | Frederick et al. | |
| 8,514,084 B2 * | 8/2013 | Yi | F24C 7/08 |
| | | | 219/254 |
| 2003/0085796 A1 | 5/2003 | Smith | |
| 2006/0059360 A1 * | 3/2006 | Ortkiese | F24C 7/08 |
| | | | 713/183 |
| 2009/0240445 A1 * | 9/2009 | Umekage | G01F 1/66 |
| | | | 702/48 |
| 2011/0035338 A1 * | 2/2011 | Kagan | G01D 4/002 |
| | | | 705/412 |
| 2012/0234915 A1 * | 9/2012 | Cappuzzo | G06F 19/327 |
| | | | 235/385 |
| 2013/0152673 A1 * | 6/2013 | Young | F23N 1/002 |
| | | | 73/40.7 |
| 2013/0214903 A1 | 8/2013 | Kalous et al. | |
| 2013/0304264 A1 * | 11/2013 | Shao | G01F 15/063 |
| | | | 700/282 |
| 2015/0108380 A1 * | 4/2015 | Huang | F16K 31/06 |
| | | | 251/129.04 |

OTHER PUBLICATIONS

PCT Search Report and Written Opinion mailed Jan. 19, 2017 for PCT Application No. PCT/US16/59763, 8 pages.

* cited by examiner

*Primary Examiner* — Vernal Brown
(74) *Attorney, Agent, or Firm* — Lee & Hayes, PLLC

(57) ABSTRACT

An apparatus may include a controller that may include one or more processors, and memory storing executable instructions that, when executed by the one or more processors, may cause the one or more processors to perform operations. The operations may include receiving key fob data from a reader. The key fob data may include ID information of a user. The operations may further include determining authorization privileges associated with the received ID information of the user, and controlling a lock system of a gas flow valve in response to the determination of the authorization privileges associated with the received ID information of the user.

20 Claims, 10 Drawing Sheets

TRACKING AND ACCESS SYSTEM

TECHNICAL FIELD

This application generally relates to a tracking and access system. More specifically, it relates to a system designed to track personnel throughout a facility and to restrict or provide access to areas within the facility or supplies located therein through the use of a tracking element.

BACKGROUND

In medical environments, such as those found in hospitals and surgery centers, it is important to maintain a safe, efficient, and secure setting to ensure the proper health and safety of staff, patients, or other personnel. Due to the rising cost of medical care and supplies used therein, medical administrators seek to minimize material waste or abuse thereof in order to maintain profitability, while, at the same time, still providing the best care possible. For example, in certain medical procedures, such as surgery, medical supplies are accessed and therein used by medical personnel. Therefore, during medical procedures, and particularly in the case of an emergency, such supplies need to be readily accessible. Alternatively, when not in use, the Medical supplies need to be safely secured and stored away. Moreover, the medical environments, such as operation rooms or particular areas of the facility, need to be safeguarded against an unauthorized user's access and use thereof.

As many medical environments are open to the public, guests, or other facility staff members, such as administrative or custodial staff, there may exist risks of 1) the spread of diseases or other harmful viruses among the various patients and staff, and 2) the misuse, abuse, and even theft of medical supplies by any person, including employees, within the medical environment. As such, managing medical supplies and users traversing throughout a facility, while also minimizing the spread of infectious diseases, represent forefront challenges for healthcare facilities and medical environments.

BRIEF DESCRIPTION OF THE DRAWINGS

The accompanying drawings, which are incorporated herein and constitute a part of this disclosure, illustrate embodiments and together with the description, serve to explain the principles of the subject of the instant application. In the figures, the left-most digit(s) of a reference number identifies the figure in which the reference number first appears. The use of the same reference numbers in different figures indicates similar or identical items.

DETAILED DESCRIPTION

Overview

Figure 1A:
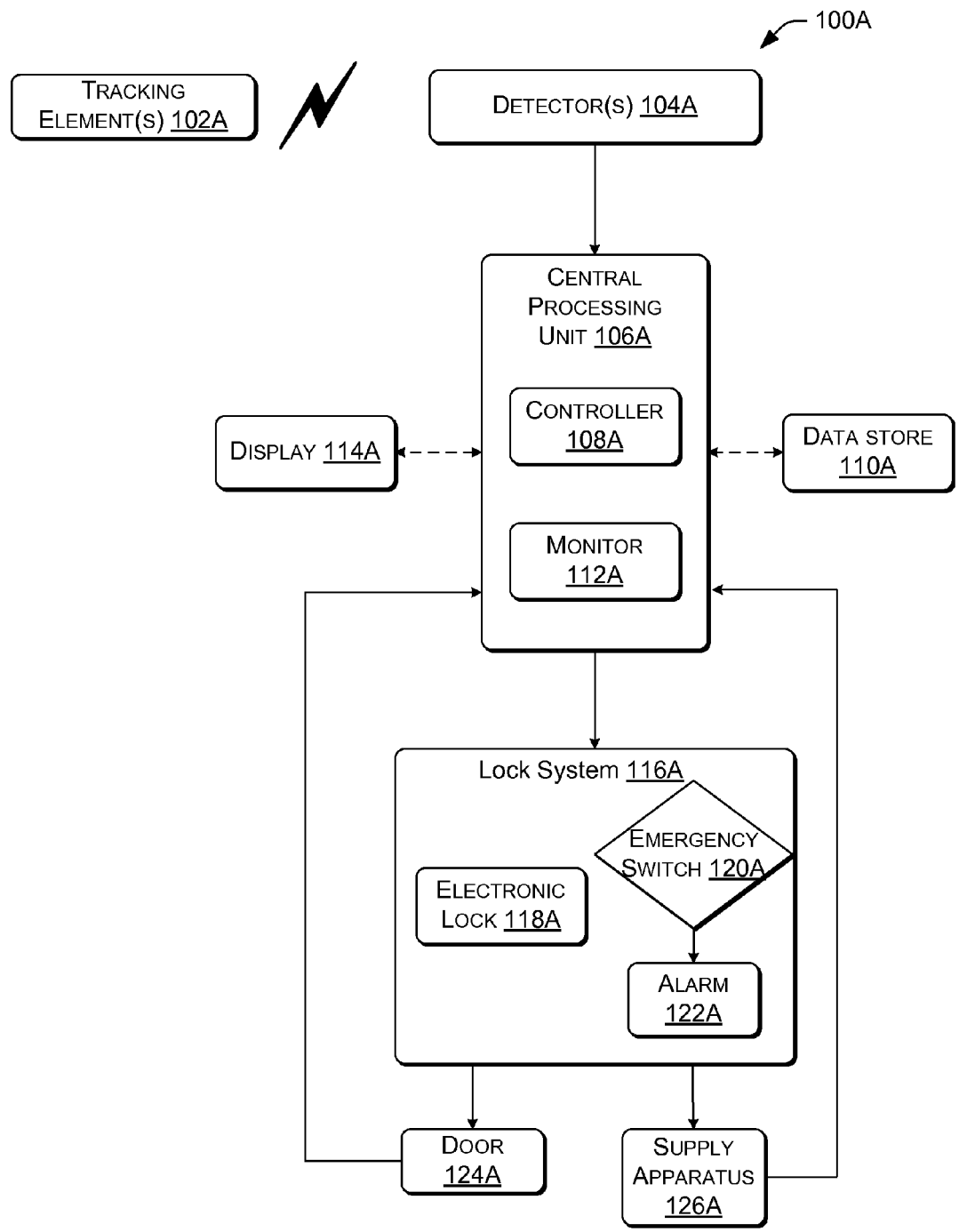
FIG. 1A illustrates a schematic of a tracking system according to an embodiment of the instant application.

This disclosure is directed to a system that may be used to monitor, track, and allow access throughout a facility, such as a healthcare facility, and to selectively allow access to supplies, such as medical supplies, including gas(es) and drugs for anesthesia, and general medication, in the example of a healthcare facility, according to the individual privileges of each individual in the facility. The embodiments herein are described with specificity in order to meet statutory requirements. However, the description itself is not intended to limit the scope of this application. Rather, the inventors have contemplated that the claimed invention might also be embodied in other ways, to include different elements or combinations of elements similar to the ones described in this application, in conjunction with other present or future technologies.

While the inventors envision many situations where the subject matter of the instant application may be implemented, a non-limiting example situation is described and illustrated herein as a specific implementation of the concept of the application. For example, in the realm of anesthesia, gases and/or anesthetic drugs, stored in drawers, containers, or the like, may be left accessible to any person entering an operating room or alternate area of a healthcare facility where such supplies are located and stored. Persons that may be expected to enter areas containing gases and/or drugs may include, for example, patients, doctors, nurses, technicians, and cleaning staff. However, as may be understood, only a portion of these personnel may be authorized to administer medications, such as, for example, the doctors. Accordingly, those authorized would need access to the supplies. Further, it is conceivable that completely unauthorized persons may enter the operating room, either accidentally or intentionally, and with or without malicious intent. Therefore, access to the areas of the facility and medical supplies located therein should be restricted to only those individuals that have proper authorization to prevent and minimize waste, misuse, abuse, and/or theft.

The tracking system described herein for implementation in a facility may generally include a tracking element for the purpose of providing a personal identification ("ID") information; a detector device to detect the tracking element; a central processing unit ("CPU") that may include a controller, a data store, and a monitor; and a lock system in communication with the CPU. A generalized description of how the tracking system may work and function are herein explained.

A person (also called a "user" or "individual" hereinafter) may be issued a tracking element that is associated with the specific person (as described below). As the person moves about the facility with the tracking element, one or more detectors may communicate with the tracking element to determine the presence or location of the person. When the person enters or attempts to enter a room or area of the facility, the detector detects the ID information of the tracking element and communicates with the CPU to determine whether the person carrying the tracking element is authorized or has privileges to access the particular area or room of the facility. For example, it is conceivable that certain areas throughout the facility may be guarded or secured to prevent access from the general public or a certain group of people.

Furthermore, with the tracking element, a determination may also and/or simultaneously be made regarding whether additional access privileges to supplies located within the area or room may be associated with the tracking element. If determined that the person has authorization for a particular room or area, and further to the supplies that may be located therein, access to the supplies may be immediately granted via communication between the CPU and the lock system. Alternatively, the tracking element may solely be implemented to access supplies and not a particular room or area of the facility, or vice versa. Accordingly, access to a particular room or supplies may be granted in tandem or separately.

Some non-limiting example embodiments of a tracking element may include: a stamp, a fob, a barcode, a card or sheet, a tag, a bracelet, or other device having embedded, encoded, imprinted, written, or otherwise associated with the tracking element, an aspect thereof that may be scanned, readable, or otherwise detectable via methods such as wireless transmission including microphone, video, RFID, electronic scanning including via a laser, or direct contact with a corresponding detector device capable of communication with the tracking element. For simplicity, the tracking element may herein be generally referred to as a "key fob." However, it is to be understood that in any instance herein where the term "key fob" is used, it may equally and/or correspondingly refer to any other form of a tracking element, including but not limited to those described above. For example, using voice recognition technology, a user's voice may be the "key fob." In some instances, using facial recognition technology, a user's face may be the "key fob."

A corresponding device that may be used to detect and communicate with the key fob may include, without limitation, a proximity-reader, a sensor, a Bluetooth or other low energy device, scanners, wireless internet systems, cameras via recognition software, magnetic and/or electromagnetic detection, or any other device that is capable of recognizing ID information of a user located on the key fob, or other tracking element, and communicating such information to the CPU. For simplicity, the corresponding device used to communicate the ID information located on the key fob with the CPU may herein be generally referred to as a "reader." However, it is to be understood that in any instance where the term "reader" is used, it may equally and/or correspondingly refer to any other form of a detector device used to detect the presence of the key fob, including but not limited to those described above.

The CPU, as described herein, may include volatile and non-volatile, removable and non-removable media implemented in any method or technology for storage of information such as computer readable instructions, data structures, program modules, or other data. Examples of a CPU may include, but are not limited to, phase change memory (PRAM), static random-access memory (SRAM), dynamic random-access memory (DRAM), other types of random-access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transmission medium that can be used to store information for access by a computing device. As defined herein, the CPU does not include transitory media such as modulated data signals and carrier waves. While embodiments of the CPU have been described herein, and will be mentioned throughout this application accordingly, it is to be understood that in any instance herein where the term "CPU" is used, it may equally and/or correspondingly refer to any other form mentioned above.

Furthermore, some non-limiting examples of the lock system may include, a magnetic lock, keyed lock, electronic lock, physical barrier, or any other device or apparatus capable of being in communication with the CPU to receive and respond to authorization privileges. In addition, the lock system may unlock and lock valves, doors, drawers, cabinets, depots, latches, devices, electronics, or any other storage mechanism/apparatus used to house, store, and/or secure supplies. It is to be understood that any instance herein where the term "lock system" is used, it may equally and/or correspondingly refer to any other form of a device used to provide and/or restrict access, including but not limited to those described above.

The key fob may be user-specific in that every person, for example, a guest, a nurse, a physician, etc., granted access or entering the facility, may be issued a key fob configured specifically to the person's respective privileges or authorizations within the facility. In some instances where the key fob is the user's voice or appearance, the user's "key fob" is recorded and stored, rather than "issued," as may be done with a separate detectable object. The respective privileges or authorizations may be, for example, according to the person's respective roles and responsibilities within the facility. For example, a doctor will likely have different roles and responsibilities, and therefore different access privileges, than a janitor or a technician.

Different key fobs may be programmed, or otherwise enabled, to permit or restrict access to a particular room or area of the facility and/or supplies, such as medical supplies, located throughout the facility. In an embodiment, the key fob may therefore provide a security measure to help prevent an unauthorized person from gaining access to a particular room or area of the facility and/or supplies that the person is not authorized to enter or obtain, respectively. For example, a healthcare facility may want to limit access an operating room. Accordingly, the healthcare facility may only provide authorization privileges for the operating room to physicians or other medical personnel.

The key fob may be in further communication with the tracking system to an extent that the tracking system may track and record the movement of, the location of, and places such as rooms visited or accessed by, a person throughout the facility, and the duration of time the person spent in the facility or each accessed room. Therefore, for every key fob specific to a person, ID information thereof may be communicated to the tracking system. For example, information communicated may include where the user is located at any instant, where the user has been, and whether the user has entered, accessed, or attempted to access any areas, rooms, or supply apparatuses of the facility. Through the tracking of users, the described tracking system may assist in tracking and monitoring problems that may otherwise be more difficult to determine a source of or solution for the problems, such as, for example, in the case of a healthcare facility, the spread of diseases, sicknesses, or viruses. Furthermore, the tracking system may provide data in analyzing and detecting patterns of inappropriate behavior, error, inaccuracies in records, and inefficiencies throughout the facility.

For example, in the instance of a healthcare facility, data may show whether a series of unexpected deaths, infections, or spread of a virus may be traced to a particular user who visited each room or area where the instance was found. Additionally, in an emergency setting, a particular doctor or nurse may be readily located throughout the facility in case of a certain need or specialty. Moreover, the healthcare facility and regulators alike may analyze the data with a perspective of risk management to protect against provider drug abuse and/or fraudulent billing.

As indicated above, depending on the authorization privileges associated with the person's key fob, the key fob may be used to provide access to supplies throughout the facility. In the above example of a healthcare facility, with respect to permitting or restricting access to medical supplies, the key fob containing ID information may be used to communicate with the CPU to provide access to medical supplies. The CPU, through the data store, may be updated with information so a user's key fob is recognized by the CPU via the reader. Accordingly, the CPU may determine the user's authorization privileges. Having been detected, the controller may determine whether the user is authorized to access medical supplies, such as, for example, anesthesia gases and/or drugs, medication, surgery equipment, and syringes. In turn, the key fob may prevent unauthorized access to medical supplies and abuse thereof by restricting access to those not recognized or authorized by the controller as having privileges.

For example, a key fob, through ID information located thereon, may identify a person as a janitor. As the janitor may not be authorized to administer medications or access medical supplies, but may have authorization to enter an operating room in order to clean, the CPU, through communication with the lock system, may unlock the door to the operation room, but not the medical supplies that may be located therein, such as the gas(es) and/or drugs. Therefore, the tracking system may prevent the malicious use of medical supplies and abuse thereof.

Within a tracking system for a healthcare facility, the CPU may be used to analyze and detect, through the ID information contained in the key fob, what doors, drawers, cabinets, and/or medical supplies, as well as quantities thereof, were used or accessed during the time an area or supply apparatus was unlocked or provided access to a user having authorization privileges. This data may be used to detect inefficiencies in medical procedures, and to determine, for example, unauthorized, unnecessarily excessive, or inappropriate uses of gases, drugs, and/or other medical supplies.

For example, in an embodiment, the data obtained through the tracking system may be analyzed to determine that user A frequently uses twice as much of the same medical supplies, such as a gas, as user B uses for the same procedure. This information may be used to investigate or determine why user A uses more medical supplies than user B for similar or like operations. Such information may be particularly relevant when it is known that procedures in which user A is involved tend to produce better, the same, or worse results than those in which user B is involved, as determined by the subsequent wellbeing of the patients. Regardless of the outcome, such information may help improve patient care and/or provide a better understanding of the facilities expenses to avoid waste where possible and to potentially save patients money as well.

Furthermore, the tracking system may support multiple users. For example, user A and user B may both be recognized by the controller as users having similar or identical authorization privileges to access to medical supplies and/or a particular room or area of the healthcare facility. Therefore, the tracking system may separately monitor the movements and accesses of user A and user B. For example, the tracking system may separately record user A as "entering" and user B as "leaving," based on a first and second detection of a reader for the users, respectively. Therefore, such system may support an entire healthcare facility's infrastructure and users and provide individual tracking of all users or persons therein.

Multiple embodiments of a system that may be used to achieve the desired effects of the instant application, including the ability to track and monitor users within a healthcare facility, are described herein below with respect to FIGS. 1A-8. It is noted that the use of the terms "a" and/or "the" with respect to any particular component described herein, is not intended to limit the quantity of that component within the invention to only one single unit, but rather there may be a plurality of the components unless otherwise explicitly stated, and the use of the terms "a" and "the" may be used for grammatical convenience.

DETAILED EXPLANATION OF THE COMPONENTS IN THE FIGURES

FIG. 1A illustrates a tracking system 100A that may include tracking element(s) 102A, detector(s) 104A, and a CPU 106A. In an embodiment, the CPU 106A may include a controller 108A, which communicates with a data store 110A. The CPU may further include a monitor 112A. The tracking system 100A may further include a display 114A and a lock system 116A. The lock system 116A may include electronic lock(s) 118A, actuatable via communication with the controller 108A, an emergency switch 120A to override electronic lock(s) 118A, and an alarm 122A for notification. The tracking system 100A may be implemented for providing access to a particular room or area or supplies by unlocking electronic lock(s) 118A based on user ID information associated with a detected tracking element 102A. To enable monitoring and tracking of users through a facility or what supplies have been accessed or used, the tracking system 100A may be in further communication with a door 124A or a supply apparatus 126A, both of which may be secured by electronic lock(s) 118A.

In an embodiment, the tracking element 102A may contain ID information specific to the user of the tracking element 102A. Prior to using the tracking element 102A, the tracking element 102A may be programmed, encoded, or otherwise associated with ID information of the user so that the detector 104A may interact and communicate with tracking element 102A. Therefore, users within the facility may all have a tracking element 102A specific to their person.

The detector 104A may be configured to communicate with the tracking element 102A. Similar to the tracking element 102A being specific to an individual, each detector 104A may be specifically associated with a particular supply apparatus and/or room or area in the facility. In some embodiments, the detector 104A of the tracking system 100A may detect the presence of the tracking element 102A. Therefore, the tracking element 102A may be detected when the tracking element 102A is presented for detection by a specific detector 104A for access to a particular room or area of the facility. Additionally, the detector 104A may detect the tracking element 102A for access to supplies.

The detector 104A may be configured to detect the ID information of the tracking element 102A through various means, including being within a predetermined distance, such as having to swipe the tracking element 102A near the detector 104A, for example, within 5 inches to 15 inches. Similarly, the detector 104A may be of a type that requires physical contact between the tracking element 102A and the detector 104A. Alternatively, the detector 104A may detect the tracking element 102A through wirelessly scanning a pre-determined and/or localized vicinity of the area around the detector 104A. Thus, depending on the security or desired applications of the facility, for example, detector(s) 104A may be altered to suit particular detecting ranges. Accordingly, multiple detectors 104A may all have a common range or individualized ranges specific to each detector 104A.

In one embodiment, for example, the limits of the scanning vicinity of the detector 104A may be defined by the physical parameters of a particular room or area of the facility. Therefore, using a detector 104A that scans a vicinity, the user may not have to physically contact or swipe the tracking element 102A directly against or within a short physical proximity of the detector 104A. Rather, as long as the tracking element 102A is within the pre-determined scanning vicinity of the detector 104A, the detector 104A may detect the presence of the tracking element 102A. Such an embodiment may be helpful when users are in a hurry and/or cannot conveniently reach or access the tracking element 102A.

In yet another embodiment, the detection of the tracking element 102A within a defined vicinity may be achieved, for example, by detecting and comparing an increment of time that it takes to send and/or receive a detection signal between the detector 104A and the tracking element 102A, with a predetermined maximum time increment (based on, for example, transmission speed capabilities of the detector 104A and tracking element 102A). If the detected increment of time is less than the maximum, the detected authorization privileges may be carried out.

Alternatively, in some embodiments, the detection of the tracking element 102A within a defined vicinity may be achieved, for example, by orienting detector 104A capable of directional detection at a known distance from the detector 104A, so as to detect the tracking element(s) 102A located within a particular direction with respect to the detector 104A. For example, a detector 104A may be on an inside wall adjacent the entrance of a particular room or area, and oriented as to face into the room, thereby detecting tracking element 102A within a particular radius or area in front of the detector 104A. As such, if the tracking element 102A passes behind the detector 104A, the tracking element 102A may not be detected inadvertently. Further, if a tracking element 102A is detected within the area covered by the directional position of the detector 104A, the detected authorization privileges may be carried out.

The detector 104A may be located at or near, either inside or outside, the entrance of a particular room or area of the facility. For example, the detector 104A may be located outside the entrance of a secured room. Accordingly, the detector 104A located outside the secured room, may be implemented to provide access to the secured room and supplies that may be located within the secured room. Likewise, it may be that there is an unsecured room, having secured supplies within the room. As such, the detector 104A may be located inside or outside the unsecured room and may provide access only to the supplies that may be located therein (as access to the room itself may not be secured). Correspondingly, a plurality of detectors 104A throughout the facility may be able to track users and safely provide access to particular rooms, areas, or supplies therein.

The detector 104A may communicate with the CPU 106A to send the ID information associated with the tracking element 102A. Using control logic, which may include hardware and/or programmed instructions, the controller 108A, the data store 110A, and the monitor 112A, may carry out the functions of the tracking system 100A. The controller 108A and the monitor 112A may include one or more processors and memory storing executable instructions to perform the desired functions, as discussed herein.

The controller 108A may determine the authorization privileges associated with the user through receiving ID information of the user associated with the tracking element 102A. As used herein, authorization privileges may refer to the particular access to supplies or areas of a facility granted to each user. Accordingly, the determination of authorization privileges may prevent unauthorized use of supplies or access to areas of the facility.

To determine authorization privileges of the user, the controller 108A may be in communication with the data store 110A. The data store 110A may be configured to store the ID information as well as the authorization privileges of a user. For example, whenever a user is granted new or different authorization privileges, the data store 110A may store such information or the previously stored information may be updated to reflect the authorization privileges associated with a tracking element 102A of a user. The controller 108A may search for the ID information received from the detector 104A and determine authorization privileges associated with the stored ID information of the user located in the data store 110A.

For example, the data store 110A may contain stored information that a user A is not authorized to access a facility's room, Room 1. Upon entering the facility, the user may be assigned tracking element 102A containing ID information that identifies the user as user A. The tracking element 102A of user A may be detected by a detector 104A for Room 1 and the detector 104A may transmit the ID information detected to the CPU 106A. From the stored information in the data store 110A, the controller 108A may determine that user A does not have authorization privileges for Room 1, and will not, therefore, control lock system 116A to unlock electronic locks 118A, so as to deny access. Likewise, since user A does not have access to Room 1, user A may not be provided access to supplies that may be located within Room 1.

The data store 110A may be updated periodically, for example, whenever a tracking element 102A is issued to a user(s). In this manner, new users may be allowed to enter the facility and traverse its interior. For example, a guest may want to visit someone in a hospital.

Furthermore, the data store 110A may be updated to alter previous authorization privileges or lack thereof. For example, keeping with the example above, user A may have authorization privileges to enter Room 1 at time B, but not at time A. Therefore, the data store 110A may be updated to indicate that user A has authorization privileges for Room 1. Accordingly, user A would be denied access at time A, but not at time B. Alternatively, the scheduled timeframes may be maintained in the data store 110A to automatically grant or deny access at certain times. This may be used, in an embodiment, to allow access to supplies during regular business hours to an employee, but the same employee may be denied access when not working, such as, for example, in the middle of the night.

Within the CPU 106A, the monitor 112A may track and record parameters of the tracking system 100A. For example, the monitor 112A may track and record the time when a detector 104A detects a tracking element 102A. Therefore, deliverable information from the detection may include: the user associated with the tracking element 102A, access or attempts to access particular rooms or areas of the facility, duration of time spent in the particular room or area, supplies accessed, and/or duration of use of the supplies accessed, etc. Such information may be used, for example, to analyze efficiencies or deficiencies with respect to what supplies a user accessed or used during an authorization period of the user.

Display 114A may be in communication with the CPU 106A. The display 114A may be, for example, an LCD screen to visually display authorization privileges of the user associated with the tracking element 102A. In an embodiment, if the detector 104A detects the tracking element 102A, the display 114A may display the ID information of the user associated with the tracking element 102A. In a further embodiment, the display 114A may display the authorization privileges of the user determined by the controller 108A.

The CPU 106A may be in further communication with lock system 116A. The lock system 116A may be controlled by the controller 108A to allow or restrict access to a particular room or area of the facility, for example, a secured room, and/or to supplies, if the controller 108A determines that the user has authorization privileges.

In an embodiment, the lock system 116A may remain locked in its resting state (when no tracking element 102A is detected), restricting access to a particular room or area of the facility or supplies. When the controller 108A determines that a user has authorization privileges, the controller 108A may communicate with the lock system 116A to provide access to, for example, a secured room or area of the facility. Additionally, access to supplies located in the secured room or area may also be provided. If the controller 108A determines that the user does not have authorization privileges, the controller 108A may communicate with the lock system 116A to maintain a locked state, thus restricting access to supplies or a particular room or area of the facility. Additionally, the controller 108A may not communicate with the lock system 116 since the resting state of the lock system 116A may already be locked.

As indicated above, lock system 116A may further include electronic lock(s) 118A, emergency switch 120A, and alarm 122A. In an embodiment, the electronic lock 118A may be actuated by controller 108A to be unlocked if the user ID information of the tracking system 102A contains authorization privileges, as determined by the controller 108A. Therefore, if the user is recognized as having authorization privileges, the controller 108A may communicate with the lock system 116A and the electronic lock 118A to provide access to supplies or a particular room or area of the facility. As shown in FIG. 1A, the electronic lock 118A may provide access via a door 124A or a supply apparatus 126A. As used herein, the door 124A may be thought of as providing access to a particular room or area of the facility, for example, doors to enter an operating room. Likewise, the supply apparatus 126A may be thought of as providing access to supplies, whether via, for example, an electronically actuated valve to access gas, or via a cabinet with lockable drawers.

In some embodiments, the sole use of an electronic lock 118A may be inappropriate or inconvenient. For example, such scenarios may include an emergency where supplies or access to a particular room or area of the facility are quickly needed. Additionally, a scenario may exist when a user with authorization privileges, as stored in the data store 110A, forgot the user's tracking element 102A. In such scenarios, access to the supplies or a particular room or area of the facility is needed but cannot be accessed through the electronic lock 118A. Therefore, an ability to override the electronic lock 118A may be needed to ensure safety and prevent adverse effects. In these scenarios, emergency switch 120A may be triggered to provide access to a particular room or area of the facility through door 124A or to supplies secured by the supply apparatus 126A. Accordingly, a user may be able to gain access to rooms or supplies even though a tracking element 102A having authorization privileges is not detected by the detector 104A.

In some embodiments, in an event where the emergency switch 120A is triggered, alarm 122A may act as a notification that an emergency or unauthorized use/access may be occurring. In an embodiment, the alarm 122A may be, for example, a visually noticeable alarm or indicator, a digital alarm, an auditory alarm, or a combination of any two or more of the foregoing types of alarm. Furthermore, the alarm 122A may be distinguishable from other alarms that might be triggered throughout the facility. Additionally, examples of visual alarms may include, but are not limited to: flashing light(s), a broken seal or tag, or a written message on display 114A. Moreover, Examples of digital alarms may include, but are not limited to: a digital communication sent to the controller 108A to begin internal monitoring and evaluation such as via video means, audio means, and/or via further scanning of a tracking element 102A having authorization privileges, and a digital communication sent to a device monitored by a person responsible for evaluating situations where emergency switch 120A is actuated. Some non-limiting examples of auditory alarms may include: a siren sound, a beeping sound, or a verbal notification via speakers located in the area of the triggered emergency switch 120A.

As an example situation, when an unauthorized use occurs by a user who lacks authorization privileges, facility administrators may be notified that an unauthorized use of supplies is occurring or that a user has entered an area or room of the facility that the user may not have authorization privileges to access. Thus, when the emergency switch 120A is triggered, the CPU 106A may activate a security system for monitoring. For example, the security system may include cameras that monitor and record the surrounding area where the emergency switch 120A was triggered.

Figure 1B:
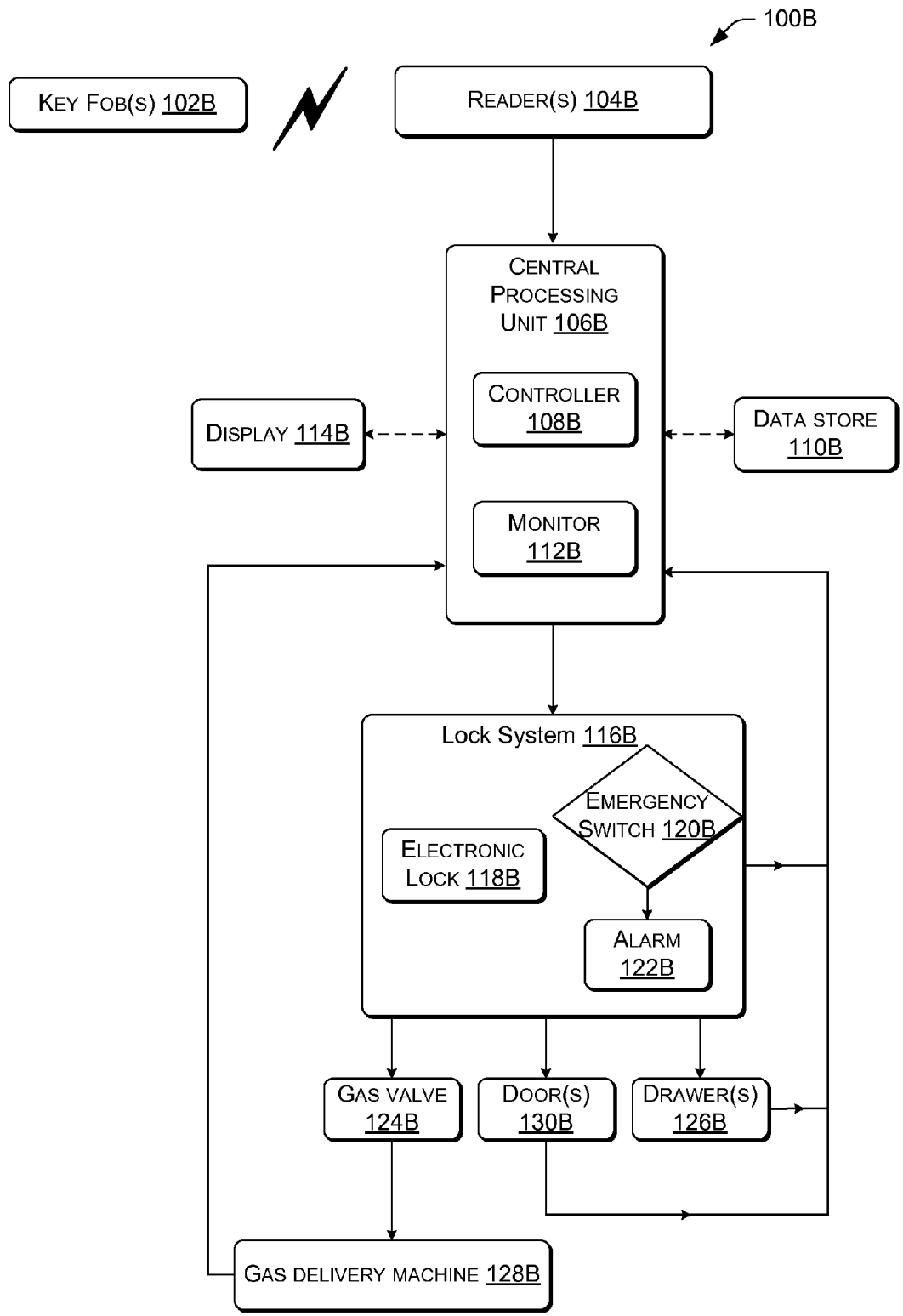
FIG. 1B illustrates a schematic of an embodiment of a medical tracking system according to the instant application.

FIG. 1B illustrates an example embodiment of a tracking system 100A, as implemented in a medical facility, with particularity to an anesthesiology setting. Specifically, medical tracking system 100B may include a key fob 102B, a reader 104B, and a CPU 106B. CPU 106B may include a controller 108B, which communicates with a data store 110B, such as the healthcare facility's Electronic Medical Record ("EMR") that is associated with the network at the facility. The CPU 106B may further include a monitor 112B. CPU 106B may be in communication with a display 114B and a lock system 116B. The medical tracking system 100B may be implemented for providing access to a particular room or area of a healthcare facility, or additionally, medical supplies, through ID information associated with key fob 102B.

In an embodiment, the medical supplies secured by lock system 116B may include, but are not limited to, anesthesia gases and/or drugs, where the gases may be coming into a room or area via a main facility line or from reserve tanks in the room, and where the drugs may be secured in drawers, cabinets, etc. Lock system 116B may include electronic lock(s) 118B, emergency switch 120B, and alarm 122B. To monitor the amounts and types of gases delivered, the drawers and cabinets accessed, or a particular room accessed, the lock system 116B may be implemented by a gas valve 124B, drawer(s) 126B, and door(s) 130B, respectively. The gas valve 124B may be further connected to a gas delivery anesthesia machine 128B, with which the gas may be properly administered to a patient. Gas valve 124B may be located on a gas line either before the line enters the machine 128B, such as the main line to the room or a supply line from the main line to the machine 128B, and/or as an internal gas valve lock inside the machine 128B, and/or an external gas lock after passing through the machine.

The reader 104B may be configured to communicate with the key fob 102B. In practice, when the user desires to access a particular room or area of the healthcare facility or obtain access to medical supplies, the user may present key fob 102B in a predetermined manner associated with the particular reader 104B of the medical tracking system 100B, whether the manner involves contact, swiping, or proximity with respect to the reader 104B, so that the reader 104B may detect the key fob 102B and read the ID information.

The reader 104B may communicate the ID information of the key fob 102B to the CPU 106B and the controller 108B may determine the authorization privileges associated with the key fob 102B. In particular, the controller 108B may determine, within the data store 110B, which may store ID information and corresponding authorization privileges of the user, for the ID information received from the reader 104B to determine whether the user's associated authorization privileges permit access to the supplies or a particular room in connection with the detector 104B.

For example, in the following situation, assume a user B is a visitor and is not authorized to access a healthcare facility's operation room. Upon entering the healthcare facility, user B may be issued key fob 102B containing ID information that identifies the user of the key fob 102B as user B. The data store 110B may be updated to indicate, amongst other privileges, that user B having key fob 102B may not be permitted access to the operation room. When user B's key fob 102B is detected at reader 104B corresponding to the operation room, the reader 104B may communicate with the CPU 106B and detect the key fob 102B as associated with user B. Based on the stored ID information in the data store 110B, the controller 108B determines that user B does not have authorization privileges for the operation room, and therefore, access may be denied. Accordingly, user B may be simultaneously restricted from medical supplies that may be found within the operation room. Alternatively, or additionally, if user B manages to enter the operation room, for instance, if the door was left open or is not secured, the detector 104B will not permit access to supplies that are locked using lock system 116B.

Monitor 112B may track and record parameters of the medical tracking system 100B. For example, in an embodiment, the monitor 112B may monitor gas flow delivered through the gas delivery machine 128B via gas valve 124B. Furthermore, monitor 112B may monitor which drawers 126B are accessed. Moreover, monitor 112B may monitor rooms or areas of the facility accessed through, for example, doors 130B. Through monitoring the gas delivery machine 128B, the drawers 126B, and the doors 130B, the medical tracking system 100B may determine where and which users, through the detection of ID information of key fob 102B, are accessing medical supplies and the quantities thereof, for example, the amount of gas used/delivered.

Display 114B may be in communication with the CPU 106B. In an embodiment, the display 114B may display the authorization privileges of the user as determined by the controller 108B, and further provide the user with an opportunity to select which types of access are desired, such as, for example, access to gases only, or the drugs in the drawers 126B as well. Additionally, the display 114B may depict how much gas or medical supplies a user has used or accessed during an authorized time period of the user.

The CPU 106B may also control the lock system 116B. The lock system 116B may be controlled by the controller 108B to allow or restrict access to medical supplies or a particular room or area of the healthcare facility if the controller 108B determines authorization privileges of the user. When the controller 108B determines that authorization privileges exist, the controller 108B may communicate with the lock system 116B to unlock or lock access to the particular room or area of the healthcare facility or supplies located therein, respectively. In an embodiment, the electronic lock 118B may provide access to the supplies or area of the healthcare facility if the ID information of the key fob 102B is associated with authorization privileges, as determined by the controller 108B through communication with data store 110B.

Emergency switch 120B may be triggered and provide access to the medical supplies or particular room or area of the healthcare facility desired to be accessed by the user, for example, during an emergency situation or where an authorized user does not have the user's key fob available. For example, if a healthcare worker, such as an anesthesiologist, needs urgent access to a gas, but does not have or cannot locate the key fob 102B, the anesthesiologist may actuate the emergency switch 120B for gas valve 124B so as to override electronic lock 118B, thereby permitting gas flow. This manner of overriding electronic lock 118B may equally apply to drawers 126B or a doors 130B into a restricted area. To assist in maintaining security, upon the emergency switch 120B being triggered, alarm 122B may be triggered.

To track and record use and access, the lock system 116B may be in communication with the monitor 112B and the data store 110B, or EMR. In an embodiment, the medical tracking system 100B may be useful for diagnostic purposes to analyze user patterns, such as how much gas a user may have administered during an operation or authorization period of the user.

As used herein, the indication of a tracking system may refer to the tracking system 100A of FIG. 1A and/or the medical tracking system 100B of FIG. 1B.

Figure 2:
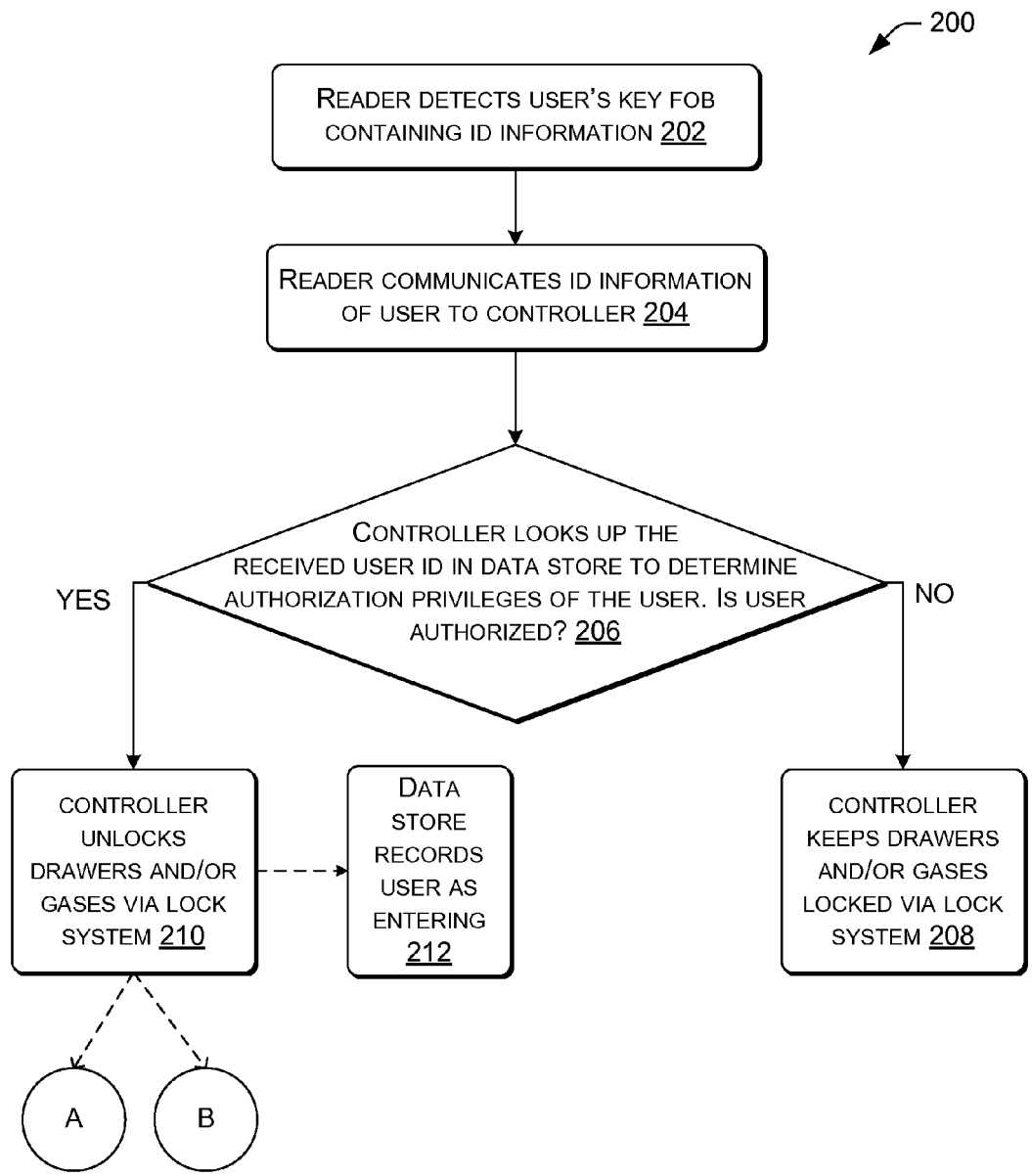
FIG. 2 illustrates a general flowchart of the embodiment of the medical tracking system of FIG. 1B through interactions with a key fob to unlock and lock access.

FIG. 2 illustrates a method 200 of providing access or restricting access based on a user's key fob (tracking element 102A and key fob 102B of FIGS. 1A and 1B, respectively). At step 202, the reader may detect the user's key fob containing ID information of the user. At step 204, the reader may communicate the ID information of the user to the controller. The controller, at step 206, may use the ID information of the user to determine whether the user has authorization privileges. Authorization privileges may be based on stored information located in a data store of a CPU. If the controller determines that authorization privileges do not exist, and therefore the user is not authorized, at step 208, the controller may communicate with the lock system to restrict access to medical supplies or areas of healthcare facility. In an embodiment, the controller may not communicate with the lock system to engage the lock system, for example, where the default state of the lock system may be locked.

If the controller determines authorization privileges of the user exist, and therefore the user is authorized, at step 210, the controller may communicate with the lock system to provide access to the medical supplies or a particular room or area of the healthcare facility that the user wishes to access. In an embodiment, at step 210, the controller may provide access to anesthesia gases or drawers which, for example, store medical supplies. As the default state of the lock system may be locked to restrict access, the controller and the lock system may communicate.

To track users throughout a healthcare facility, the method 200 may include step 212 whereby the user is recorded as entering a room or particular area, based on a first scanning by the reader and subsequent unlocking by the controller.

As a user may be provided access to medical supplies or particular room or area of the healthcare facility, the user may be able to use the supplies or traverse the particular area of the facility. For example, a doctor may be issued a key fob for use when the doctor enters the healthcare facility for work. When the doctor enters an operation room where an operation is to be performed by the doctor, the reader for the operation room may detect the doctor's key fob and provide access to the room and/or supplies located therein. Alternatively, the doctor may not be provided access when an operation is not scheduled to be performed.

Subsequent to using supplies or a room or particular area, or if an expected duration of time for the user to stay is exceeded, to prevent unauthorized or malignant uses of the healthcare facility and medical supplies located therein, the lock system may engage.

Figure 3A:
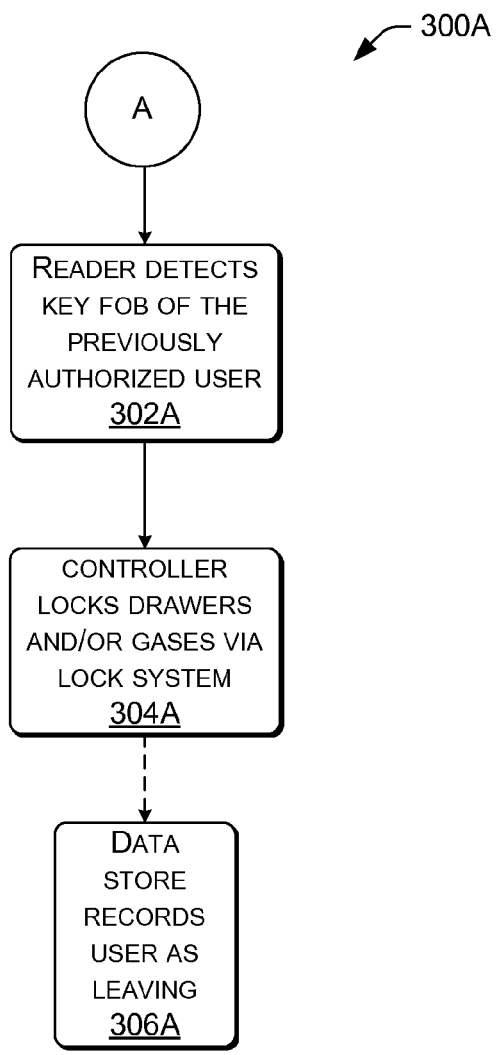
FIG. 3A illustrates a flowchart of a subroutine in the embodiment of the medical tracking system of FIG. 1B when the system detects the key fob of a previously authorized user.

Illustrated in FIG. 3A, method 300A depicts an example embodiment (A) of a continuation of method 200 of FIG. 2. Specifically, method 300A shows the flow of a detection by the reader of a previously authorized user, where "previously authorized user" refers to a user determined to have a key fob with authorization privileges in step 206 of FIG. 2. At step 302A, the reader may again (having already detected a first time) detect the key fob of a previously authorized user. To prevent access to subsequent users, whether having authorized privileges or not, at step 304A, the controller may communicate with the lock system to restrict access to the medical supplies or an area or particular room of the healthcare facility. Therefore, in some instances, the medical tracking system (of FIG. 3A) may be implemented as a "check-in (entering), check-out (leaving)" process. This process may: 1) provide a security measure to restrict access to a person who does not have authorization privileges; 2) prevent abusive or unauthorized use or access; and 3) increase productivity/utilization of a room's block time by surgeons, such as in an operating room.

Additionally, as indicated by the dashed line in step 306A, the data store, such as the EMR at the facility, may record the user's time of entry and departure from the room or area of the facility automatically, if so desired. In conjunction with step 212 of FIG. 2, step 306A may be helpful to track and record the movement and efficiency of a user throughout a facility. Further, the data in the EMR may be useful to determine errors or fault that relates to liability issues.

For example, if the controller determines that authorization privileges of the user exist, the controller may communicate with the data store that the user is entering and the user is provided access (FIG. 2 at step 212). When the user's key fob is detected by the reader a second time, for example, when a doctor has finished an operation and wishes to leave, the user is detected as a previously authorized user (step 302A). Accordingly, the controller may lock access to supplies or the room to prevent unauthorized or malignant uses thereafter (step 304A). Thus, when the user is detected by the reader, the monitor communicates that the user is leaving, and the data store may record the user as leaving (step 306A).

Figure 3B:
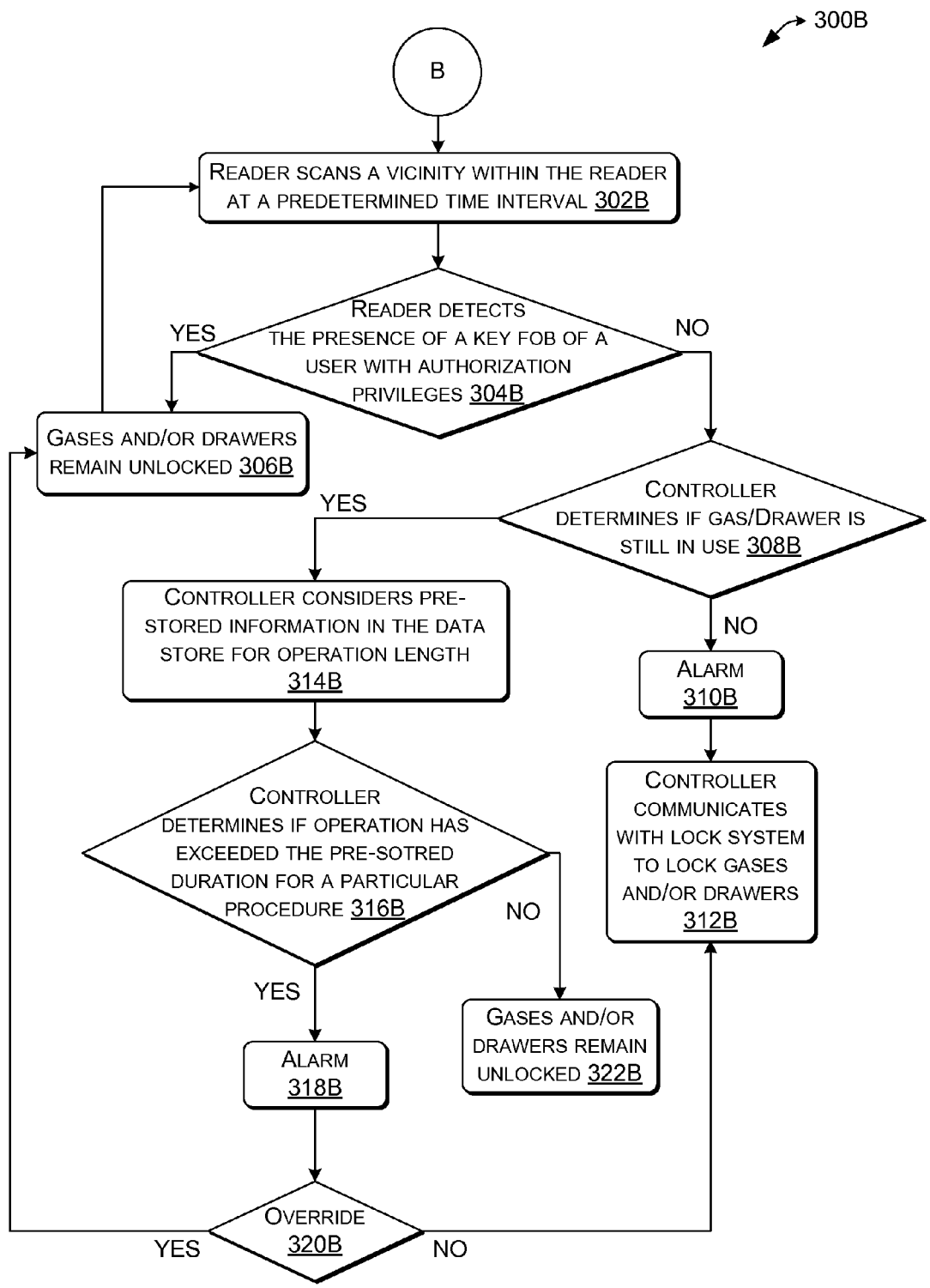
FIG. 3B illustrates a flowchart of an alternative subroutine in the embodiment of the medical tracking system of FIG. 1B when the system detects the key fob of a previously authorized user.

FIG. 3B depicts method 300B as an alternative embodiment (B) of a continuation of method 200 of FIG. 2. Specifically, method 300B shows the flow of the tracking system wherein the reader scans a localized vicinity near the reader. At step 302B, the reader may scan a vicinity near the reader at a predetermined time interval. For example, the predetermined time interval may be predetermined by facility administrators and implemented by the CPU 106A, 106B. For example, the predetermined time interval may be in the realm of seconds, minutes, hours, or any combination thereof. At step 304B, by scanning for a key fob, the controller may determine whether the reader detects the presence of a user with authorization privileges. If the reader detects the presence of a key fob of a user with authorization privileges, at step 306B, access to the medical supplies or area of the facility may remain unlocked because a user with authorization privileges is detected. In an example embodiment, the medical supplies may include gases or drawers.

If, at step 304B, the reader does not detect the presence of a key fob with authorization privileges, at step 308B, the controller may determine if the gas or other supplies are currently in use. Step 308B may assist in ensuring the safety of the healthcare facility and its users. For example, although a user with authorization privileges is not detected, access to the medical supplies may be needed, for instance, in the case of an emergency.

If the medical supplies are not in use, the tracking system may trigger an alarm 310B which may warn any users or personnel with the area that access to the medical supplies may be restricted. For example, in an embodiment, restriction may be implemented through a timer. The alarm 310B, may be, for example, auditory and/or visual. The alarm may warn potential users to trigger the emergency switch, in order to keep access (discussed previously), rather than having access to the supplies restricted, thereby potentially avoiding adverse effects.

At step 312B, the controller may communicate with the lock system to lock access to the medical supplies as a user with authorized privileges was not detected and the medical supplies are not in use. Therefore, in some instances, access may be restricted if the reader does not detect the presence of an authorized user in order to assist in reducing the abuse of medical supplies by users not having authorization privileges.

In an illustrative example situation where 1) an operation was scheduled or is occurring, 2) the reader previously unlocked access to the gases and drawers for an authorized user (step 210), and 3) if the controller determines that the gases and drawers are in use at step 308B, the controller may proceed to step 314B, wherein the controller may consider stored information in a data store. Stored information may include, for example, the expected or usual duration of time for an operation or other procedure being performed in the accessed operation room. As such, the tracking system may identify how long the authorized user is expected to require access to the medical supplies. Having determined the operation or procedure length at step 314B, the controller at step 316B may determine if the current duration of access has exceeded the pre-stored expected duration for the particular operation. In some instances, the data store may store different pre-stored expected durations and/or expected quantities or concentrations of supplies for different operations, which data may further account for the different biological aspects of different patients.

The current duration of access may be accomplished by tracking a time since the reader first detected the user's key fob, or alternatively, for example, tracking the length of time that the gases have been provided access. If the controller determines that the duration of the current access to supplies or flow of gas has exceeded the pre-stored duration (or expected quantity) for the particular procedure, an alarm 318B may be triggered. The alarm 318B may indicate and warn users and/or administrators of the facility that a potential unauthorized or malignant use is underway because of the abnormal excess of time (or quantity) of the current access or flow of gas.

If the alarm 318B is triggered, an individual accessing the supplies may have the opportunity to override the alarm at step 320B by actuating an emergency switch, for example, so as to maintain access, whereby the process resets to step 306B and the gases and drawers remain unlocked. Alternatively, if no override occurs in step 320B, access to the gases or medical supplies may be restricted, as in step 312B.

It is recognized that the current duration of access or quantities of supplies used therein may exceed the pre-stored expected operation length, expected duration of access, or limits for many reasons, such as a complication during an operation. Therefore, the possibility of an override 320B may be included, whereby the user or person, who is about to be restricted from access, is able to continue having access to the medical supplies through step 306B. Note that the override at step 320B may be, for example, the emergency switch 120A or 120B, or another form of override capability, within the tracking system 100A of FIG. 1A or medical tracking system 100B of FIG. 1B.

Alternatively, if it is determined that the current duration of privileges has not exceeded the pre-stored operation time length at step 316B, access to the medical supplies may remain available at step 322B.

In an illustrative embodiment, method 300B of FIG. 3B may be considered a "hands-off" system, whereby the user does not have to manually and/or continuously scan the user's key fob against or in a close proximity to the reader. Some potential advantages of method 300B may include situations such as, for example, when the user is involved in an operation and may not have the time to manually scan, or may not want to be locked out and/or restricted from access to the medical supplies.

Additionally, by determining if the current duration of access exceeds the pre-stored operation length, the tracking system may determine inefficiencies associated with medical procedures. Similarly, the tracking system may associate inefficient uses with specific users which may be used to increase the health and safety of patients and provide for a more efficient use of medical supplies through a healthcare facility.

Figure 4:
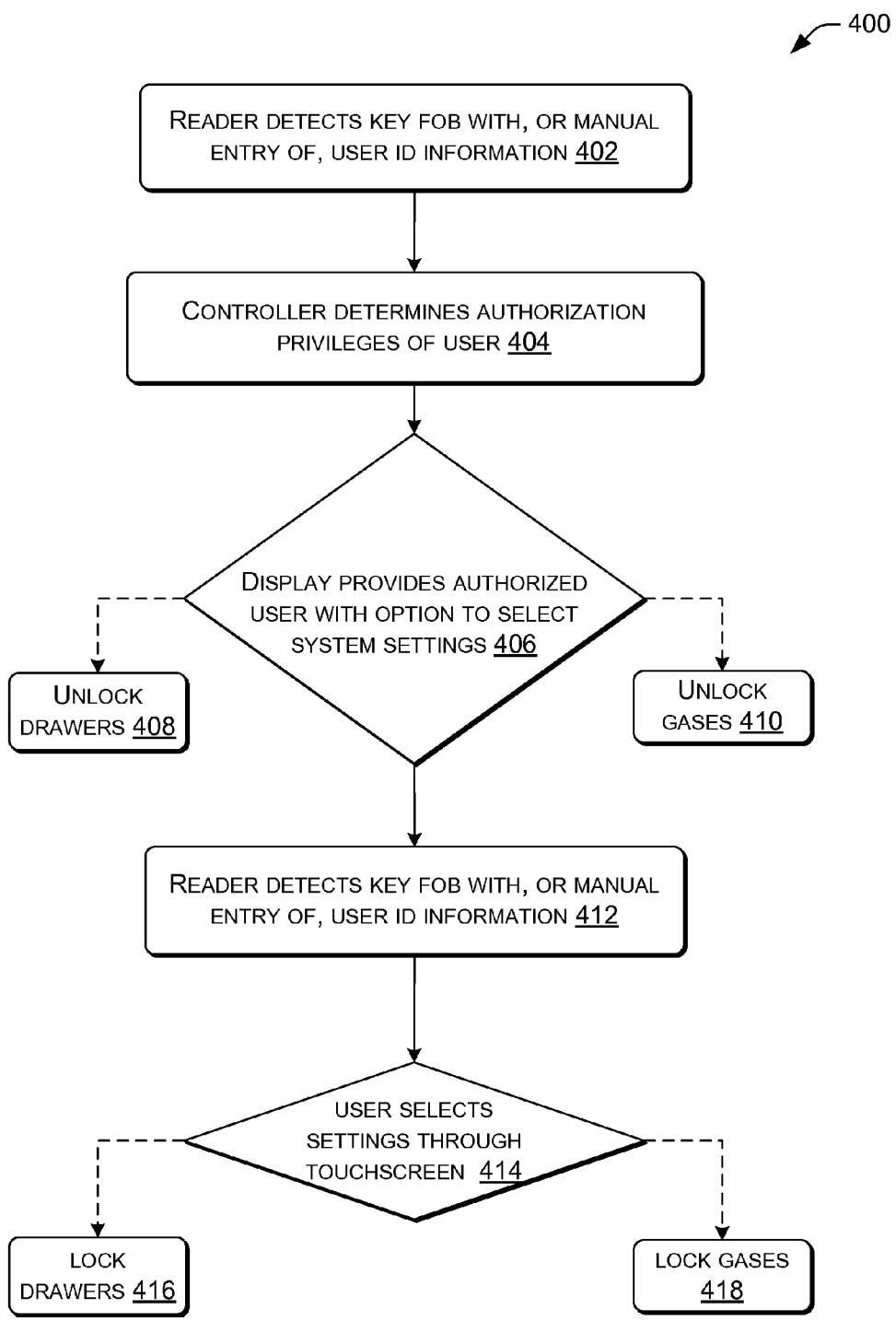
FIG. 4 illustrates a flowchart in an embodiment of the medical tracking system using a touchscreen.

In FIG. 4, an example embodiment of a tracking system process 400 is shown in which a touchscreen is incorporated to carry out some of the functions of the tracking system. In some instances, an interactive display, such as the aforementioned touchscreen, may be used to display settings and to allow users to manage an authorized access.

At step 402, the reader may detect ID information of a user's key fob. The controller may determine, at step 404, authorization privileges of the user and display, through the touchscreen, settings of the tracking system. The controller may determine authorization privileges, for example, via communication with a data store having pre-stored information (as discussed previously).

For example, although a user may have many authorization privileges, the user may not want or need to access all medical supplies but rather, in some instances, the user may desire to access only a particular room in the healthcare facility or access certain supplies therein. Therefore, rather than providing access to all medical supplies based on, for example, pre-stored information, the display of the touchscreen may provide an authorized user with an option of unlocking certain supplies for access, at step 406. As such, the user may, via the touchscreen, elect to unlock drawers in step 408, and/or unlock gases in step 410. Further, the user may update the selections at a later time by interacting with the touchscreen again.

In a further embodiment, a touchscreen may be located outside a door to a particular room or area of the facility. Through the touchscreen, the user may select to unlock access to the room (if the user has authorization privileges), while maintaining the supplies located within the room locked.

At step 412, the reader may detect the key fob of an authorized user (which may be the previously authorized user that first accessed the system, or another authorized user, who may be assisting or has other needs). When the user is finished accessing the medical supplies, after detection of the key fob in step 412, the display of the touchscreen may provide the user with an option of locking the supplies that were accessed, at step 414. As such, the user may, via the touchscreen, elect to lock drawers in step 416, and/or lock gases in step 418. In the event that the user had selected to unlock a room or area of the facility, the user may select to lock access to the particular room or area of the facility as well.

Accordingly, by restricting access of particular aspects of the facility to particular people, the medical tracking system may prevent access to unauthorized users and potential abuses thereof.

Additionally, embodiment 400 may be useful in applications where a user is observing or supervising several areas or rooms of a healthcare facility. For example, in anesthesia, an anesthesiologist may supervise different rooms throughout the healthcare facility. Upon leaving one room, however, the anesthesiologist may want to keep access to the medical supplies for others that may be located therein, for example another user who is able to administer anesthesia. In doing so, the anesthesiologist, who is an authorized user, may select through the touchscreen to keep access to medical supplies open.

In an embodiment, in a situation where the authorized user has a need to leave unexpectedly from a room where supplies were accessed, upon leaving the room, the user may place the selected settings on a timer, so that if the user with authorization privileges does not return in the specified time, access to the supplies may be restricted. Accordingly, abuse of medical supplies may be prevented by restricting access.

In some instances, the authorized user may manually enter the user's ID information via the touchscreen. For example, if the authorized user does not have his or her key fob, but still needs access to medical supplies or an area of the healthcare facility. Accordingly, the tracking system may authorize the user (based on the entered ID information) and may display settings to allow the user to select system settings (step 406).

Figure 5:
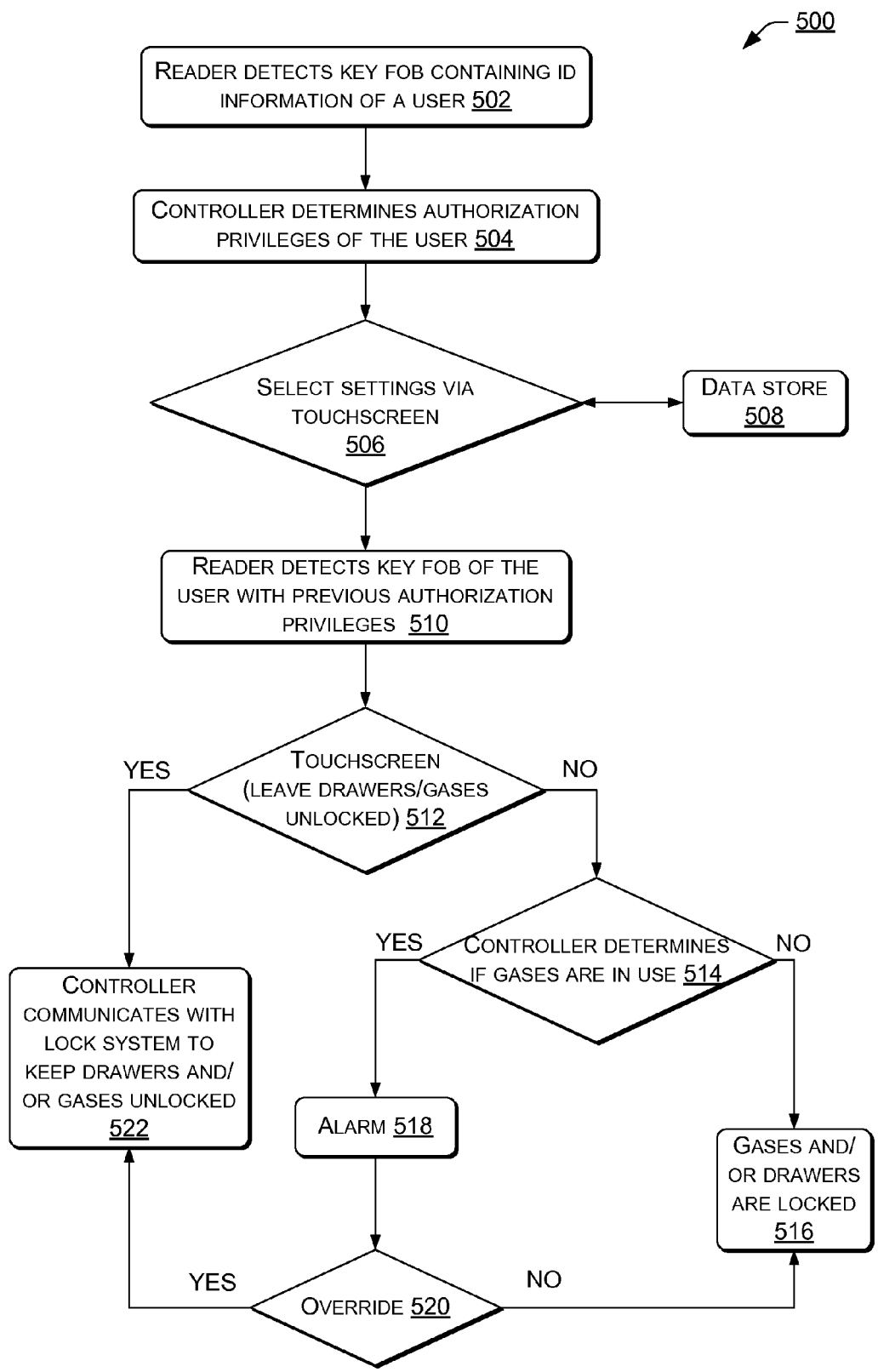
FIG. 5 illustrates a flowchart of another embodiment of the medical tracking system using a touchscreen.

FIG. 5 illustrates an example embodiment of a method 500 of a tracking system of with a touchscreen and an override function. At step 502, the reader may detect the key fob containing ID information of a user. At step 504, the controller may determine authorization privileges of the user. At step 506, and as similarly described in detail in FIG. 4, the user may select system settings through the touchscreen. Accordingly, the user's selection(s) may be communicated to the data store at step 508 to record and monitor the selections of the user.

At step 510, the reader may detect the key fob of the previous user with authorization privileges. The user may select settings at step 512 through the touchscreen, such as selecting to leave access to the gases or drawers. If the user with previous authorization privileges does not want to leave access to the gases or drawers open, and therefore desires to restrict access, the controller may determine at step 514 if the gases are still in use. Accordingly, this step may assist to prevent restricting access to gases that may be required or needed during an operation.

If the controller at step 514 determines that the gases or other medical supplies are not in use, the gases may be restricted access at step 516. As such, locking of the gases and other medical supplies may assist in preventing unauthorized or abusive uses thereafter. Additionally, the restriction of gases or other medical supplies may be associated with a timer whereby access is restricted after a predetermined interval.

Alternatively, if the controller at step 514 determines that the gases are still in use, the tracking system may trigger an alarm at step 518 to indicate to users and/or administrators that a user has selected to restrict access. For example, the alarm 518 may be an auditory and/or visual alarm. Step 518 may assist in preventing the user from restricting access needed by the patients, for example, if a user accidently selected to lock access to the gas(es). If the alarm at step 518 is triggered, the user may override an impending restriction at step 520. At step 520, the user may either choose to override access, for example, via the emergency switch of the tracking system, or to not override access, thereby locking the gases and/or drawers at 516.

If the user overrides the lock to leave unlocked the access to the gases or drawers at step 520, the controller may communicate with the lock system to keep the drawers and/or gases unlocked at step 522.

FIGS. 6A-6D illustrate, via a sequence of schematics, a process of access to supplies in a room having restrictions, where the tracking system implemented in the room schematics includes a reader that scans a defined area (either continuously or at predetermined intervals of time) to determine whether access should be granted, continued, or locked. For example, the area may be a particular room of a healthcare facility, such as, an operating room.

Figure 6A:
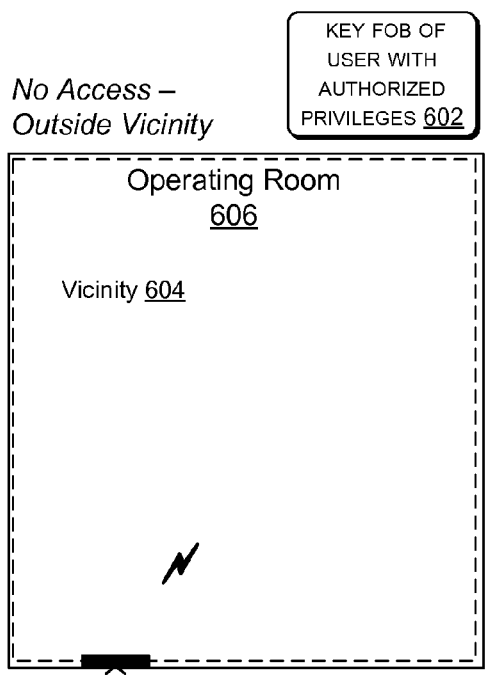
FIG. 6A-6D illustrate various stages of access according to an embodiment of a medical tracking system apparatus in relation to the location of a key fob according to the instant application.

Shown in FIG. 6A, the key fob of a user with authorized privileges 602 is located outside a vicinity 604 of an operating room 606 having a reader 608 located therein. The scannable vicinity is delineated by the dashed lines bordering the walls of the room 606. When the reader 608 scans the vicinity 604, the reader 608 may not detect the key fob of the user with authorized privileges 602, since the fob is outside the vicinity 604. Thus, when the reader 608 does not detect a key fob of a user with authorized privileges 602 within the dashed-lined area, (e.g., the user walks by the room outside) the tracking system does not unnecessarily unlock medical supplies located therein.

Figure 6B:
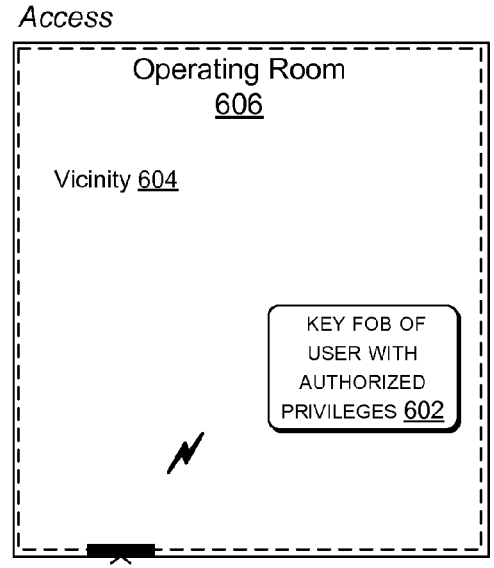

In contrast, in FIG. 6B, the user having a key fob with authorized privileges 602 has entered the room 606, and is now located within the vicinity 604 of the reader 608 in an operating room 606. Therefore, when the reader 608 scans the vicinity 604, the reader 608 may detect the key fob of the user with authorized privileges 602. In turn, the authorized user may be provided access to medical supplies located therein.

Figure 6C:
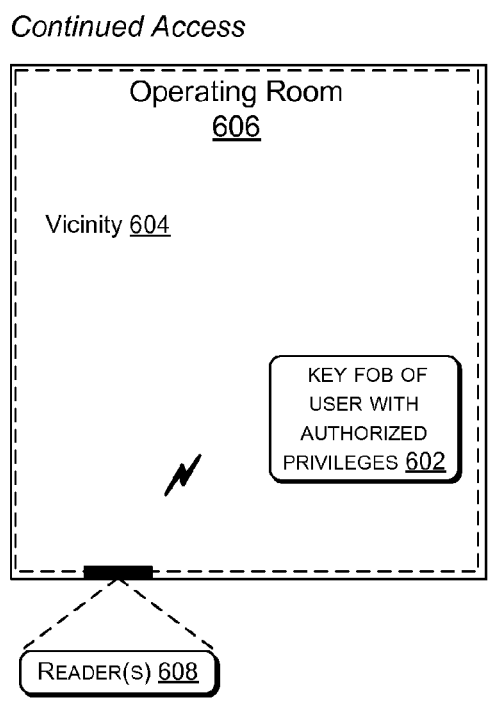

In FIG. 6C, the key fob of the user with authorized privileges 602 is still located within the vicinity 604 of the reader 608. When the reader 608 scans the vicinity 604 again, the reader 608 may detect the key fob of the user with authorized privileges 602 again and the supplies remain unlocked. In particular, FIG. 6C illustrates that, so long as the key fob of a user with authorization privileges 602 is detected within the vicinity 604 by the reader 608, access to the supplies may be continued.

Figure 6D:
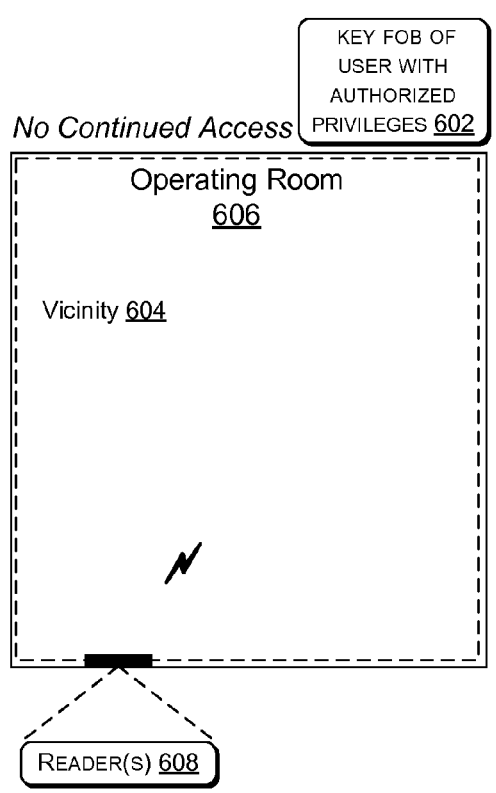

However, as illustrated in FIG. 6D, when the key fob of the user with authorized privileges 602 is no longer detected in the vicinity 604, the supplies may be locked again. Thus, the system reverts back to a similar state as depicted in FIG. 6A. As such, when the reader 608 scans the vicinity 604 within the reader 608, the reader 608 will not detect the key fob of the user with authorized privileges 602.

In further embodiments and as discussed previously, the vicinity 604 may be altered to embody a certain area within the operating room 606. For example, the vicinity 604 may extend to the physical boundaries of the operating room 606, or the vicinity 604 may entail a prescribed area surrounding the reader 608, as discussed previously.

Figure 7:
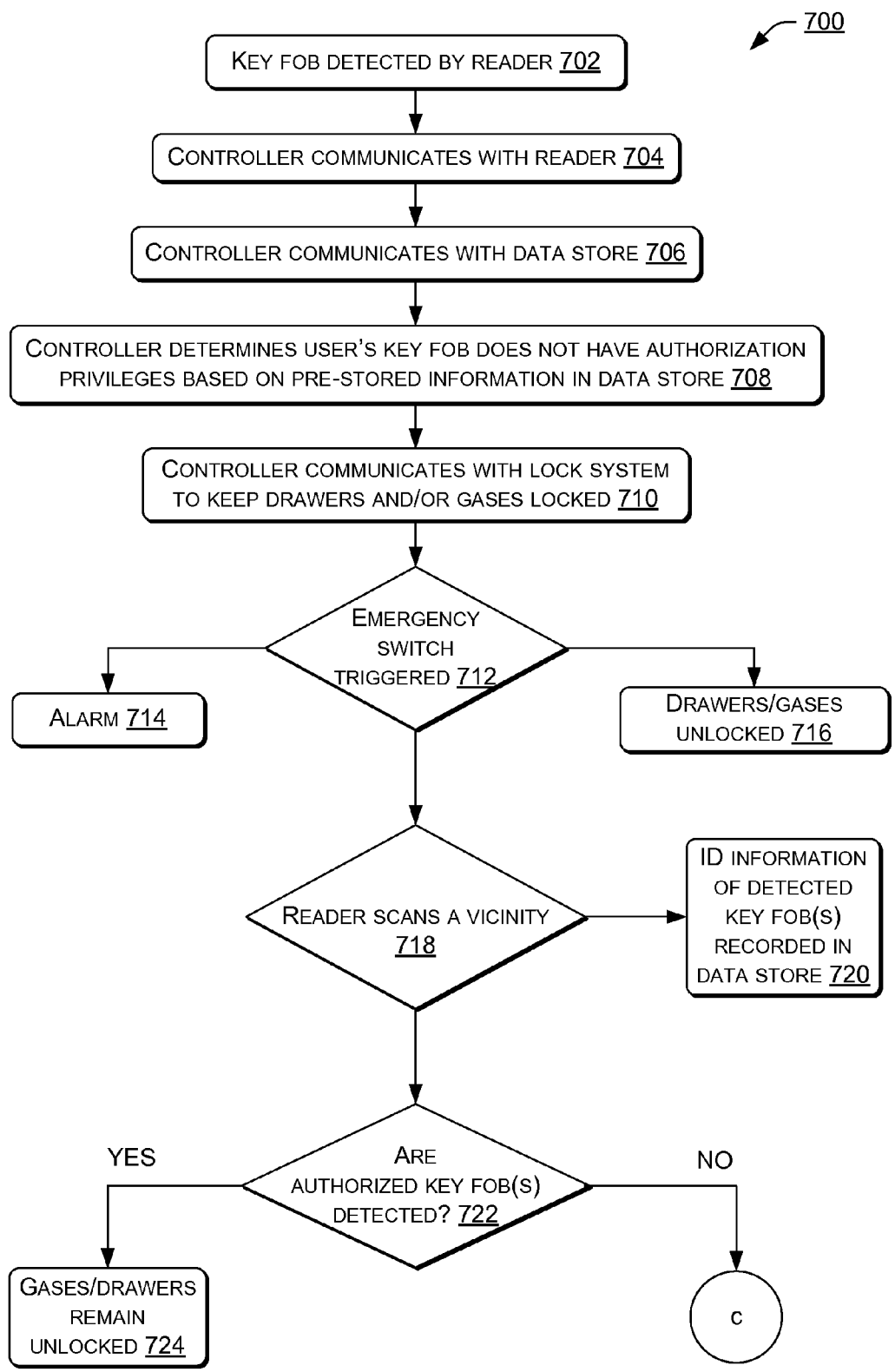
FIG. 7 illustrates a flowchart of an embodiment of a medical tracking system when an emergency switch is triggered.

FIG. 7 illustrates a method and response 700 when an override switch or emergency switch of the tracking system is triggered.

In an embodiment, when a key fob is detected by the reader at step 702, the controller may communicate with the reader at step 704. The controller may communicate with the data store at step 706 and determine, at step 708, that the user's key fob does not have authorization privileges based on the pre-stored information in the data store. Thus, the controller communicates with the lock system to keep the supplies locked, and the user is not provided access, step 710.

However, it is recognized that in some instances, access to the drawers, gases, or other medical supplies and devices may be needed or required for urgent health concerns. For example, at step 712, the emergency switch may be triggered to allow access to the drawers, gases, or other medical supplies, despite a previous denial of access due to the absence of a key fob having authorized ID information.

When the emergency switch is triggered at step 712, several things may occur. An alarm may be triggered 714 to indicate the presence of an emergency or that an unauthorized use of the medical supplies may be occurring. The alarm may be auditory and/or visual. Furthermore, when the alarm is triggered at step 714, the medical supplies, such as the gases and/or drawers, may be unlocked, at step 716. In some instances, access to the medical supplies may only last for a predetermined amount of time to allow an authorized user to prove the need for access. Additionally, the reader may scan the vicinity 718 to determine whether any key fob of any user is present. If a user key fob is detected, ID information of the user's key fob may be recorded in the data store at step 720. The recording of the key fob may allow the tracking system to record which user(s) was responsible for triggering the emergency switch in step 712. The healthcare facility then has the ability to analyze the recorded data.

In step 722 of FIG. 7, the tracking system may determine whether any detected fobs belong to a user having authorization privileges. If an authorized user is detected, the tracking device may leave the gases/drawers unlocked, at step 724. Alternatively, the reader may detect no authorized key fobs at step 722, at which point, the method 700 goes to the steps in "c," which are described with respect to the steps of method 800 in FIG. 8.

Figure 8:
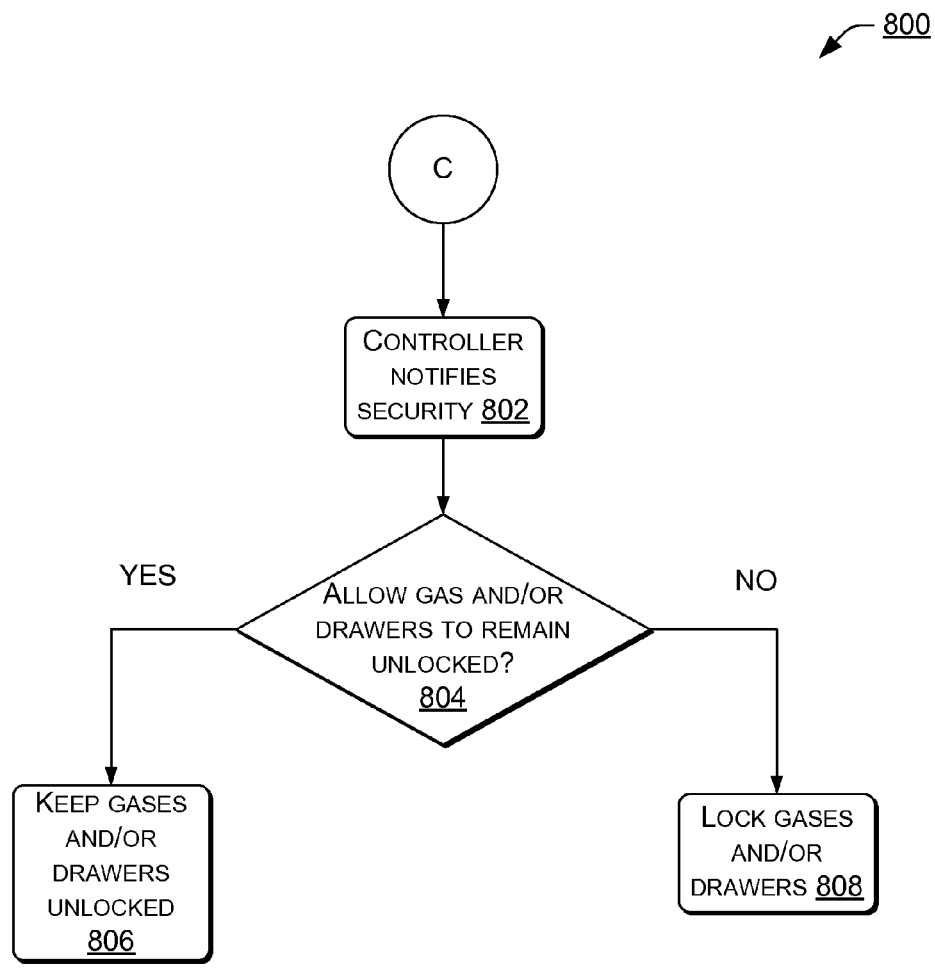
FIG. 8 illustrates a flowchart of a further functionality of the embodiment of the medical tracking system of FIG. 7.

As illustrated in FIG. 8, when no authorized key fobs are detected in step 722 of FIG. 7, the tracking system may notify security personnel (and/or healthcare facility administrator) at step 802. In some instances, the notification may come as a text message, cellular call, email, or security camera video footage. Further, the security personnel/administrator may determine whether to allow or restrict access to the medical supplies at step 804.

Thus, in an embodiment, a user with authorization privileges may have forgotten the user's key fob to provide access to the medical supplies. While the user may not have the key fob, the user may be otherwise authorized to access the medical supplies, according to the stored data. Regardless, when a user (authorized or not) activates the emergency switch (step 712 of FIG. 7), security may be notified 802. In some instances, a facility implementing the tracking system may have security cameras placed throughout the facility. In the event an emergency switch is activated, one or more security cameras may be used to provide a view of the location where the triggered emergency switch was activated. Accordingly, an administrator or security member may view the location remotely via video feed from the security cameras to determine whether the individual who triggered the emergency switch is an authorized user having authorization privileges. If determined that the individual has authorization privileges and there appears to be a legitimate use of the supplies, the administrator or security personnel may ignore the notification (or may deactivate an alarm should there be one) and leave the medical supplies, such as the gases or drawers, unlocked, at step 806. If determined, however, that the individual is not authorized to access the medical supplies, the administrator or security personnel may initiate a process of locking the medical supplies at step 808. In an embodiment, the administrator or security personnel may access the tracking system, either remotely or directly, and may override the controller so as to have the tracking system lock the supplies.

In alternative embodiment of the described example, having been notified at step 802, the administrator/security personnel may physically examine the area where the emergency switch was triggered and may make a decision whether to restrict or continue access to the medical supplies. However, in an embodiment, access to the medical supplies may remain otherwise unlocked.

CONCLUSION

Although several embodiments have been described in language specific to structural features and/or methodological acts, it is to be understood that the claims are not necessarily limited to the specific features or acts described. Rather, the specific features and acts are disclosed as illustrative forms of implementing the claimed subject matter.

What is claimed is:

1. An apparatus for controlling a lock mechanism on a gas flow valve in a facility, comprising:
    a controller including:
        one or more processors, and
        memory storing executable instructions that, when executed by the one or more processors, cause the one or more processors to perform operations including:
            receiving key fob data from a reader, the key fob data including ID information of a user,
            determining authorization privileges associated with the received ID information of the user, and
            controlling the lock mechanism on the gas flow valve in response to the determination of the authorization privileges associated with the received ID information of the user, such that:
                when determined that the user is not an authorized user, the one or more processors further perform an operation of maintaining the lock mechanism in a locked state to prevent gas flow, and
                when determined that the user is an authorized user, the one or more processors further perform an operation of unlocking the lock mechanism to an unlocked state to allow gas flow,
            wherein, in response to activation of a manually activated emergency switch, which is configured to allow the user to override the lock mechanism on the gas flow valve to unlock the gas flow valve, the one or more processors further perform an operation of activating an alarm to notify facility personnel of the activation of the emergency switch.

2. The apparatus according to claim 1, further comprising a monitor in communication with the controller,
    wherein, when the executable instructions are executed by the one or more processors, the one or more processors perform further operations including causing the monitor to:
        monitor a usage of gas from the gas flow valve, and
        record the usage of gas as used by the user associated with the ID information from the key fob data.

3. The apparatus according to claim 2, wherein the monitor is in further communication with a gas delivery machine.

4. The apparatus according to claim 3, wherein the usage of gas as recorded by the monitor includes at least one of:
    an amount of the gas delivered via the gas delivery machine, or
    a flow of the gas delivered via the gas delivery machine.

5. The apparatus according to claim 2, wherein, when the executable instructions are executed by the one or more processors, the one or more processors perform further operations including causing the monitor to record information communicated between the reader and the controller.

6. The apparatus according to claim 1, further comprising a data store in communication with the controller, the data store having storage space for storing a record of the ID information of the user and the authorization privileges associated with the ID information of the user.

7. The apparatus according to claim 1, wherein, when the executable instructions are executed by the one or more processors, the one or more processors perform further operations including controlling access to medical supplies via a lock mechanism on at least one of a drawer or a cabinet door in response to the determination of the authorization privileges associated with the received ID information of the user.

8. The apparatus according to claim 6, further comprising a lock system including
    the lock mechanism on the gas flow valve, and
    the lock mechanism on the at least one of the drawer or the cabinet door.

9. The apparatus according to claim 1, wherein, when the executable instructions are executed by the one or more processors, the one or more processors perform further an operation of, after facility personnel have been notified of the activation of the emergency switch, determining whether to allow the gas flow valve to remain unlocked.

10. The apparatus according to claim 1, further comprising a touchscreen display to display setting options to the user.

11. A system for controlling a lock mechanism on a gas flow valve in a facility, comprising:
  a reader configured to read ID information of a user;
  a lock system including a lock mechanism on a gas flow valve;
  a controller including:
    one or more processors, and
    memory storing executable instructions that, when executed by the one or more processors, cause the one or more processors to perform operations including:
      receiving ID information of the user from the reader,
      communicating with a data store to determine authorization privileges associated with the received ID information of the user, and
      controlling the lock mechanism on the gas flow valve in response to the determination of the authorization privileges associated with the received ID information of the user, such that:
        when determined that the user is not an authorized user, the one or more processors further perform an operation of maintaining the lock mechanism in a locked state to prevent gas flow, and
        when determined that the user is an authorized user, the one or more processors further perform an operation of unlocking the lock mechanism to allow gas flow;
  a manually activated emergency switch configured to allow the user to override the lock mechanism on the gas flow valve to unlock the gas flow valve; and
  an alarm configured to be triggered in response to activation of the emergency switch and to notify facility personnel of the activation of the emergency switch.

12. The system according to claim 11, further comprising a tracking element including the ID information of the user.

13. The system according to claim 12, wherein the tracking element is an electronic device having the ID information of the user encoded therein.

14. The system according to claim 11, wherein, when the executable instructions are executed by the one or more processors, the one or more processors perform further operations including recording in the data store:
  a first receipt of the ID information from the reader as the user entering a room to access medical supplies, and
  a second receipt of the ID information from the reader as the user leaving the room.

15. The system according to claim 11, wherein when the executable instructions are executed by the one or more processors, the one or more processors perform further operations including:
  scanning, via the reader, a predetermined vicinity within an area adjacent the reader to determine whether the authorized user is detected within the vicinity, and
  communicating with the lock system to maintain the gas flow valve in an unlocked state in response to a determination that the authorized user is detected within the vicinity.

16. The system according to claim 15, wherein, in response to a determination that the authorized user is not detected within the vicinity, when the executable instructions are executed by the one or more processors, the one or more processors perform further operations including at least one of:
  determining whether gas is still in use, and communicating with the lock system to maintain the gas flow valve in an unlocked state in response to a determination that the gas is still in use, or
  determining whether a duration of gas use has exceeded an expected duration, and triggering the alarm in response to a determination that the duration of gas use has exceeded the expected duration.

17. The system according to claim 11, further comprising a touchscreen display to display setting options in response to a determination that the ID information of the user indicates an authorized user.

18. A lock system for gas control in a facility, comprising:
  a lockable electronic gas flow control valve configured to connect to a gas supply;
  a controller communicatively coupled to the gas flow control valve, the controller including:
    one or more processors, and
    memory storing executable instructions that, when executed by the one or more processors, cause the one or more processors to perform operations including:
      receiving ID information of a user,
      determining whether the ID information indicates that the user is authorized to unlock the gas flow control valve, and
      unlocking the gas flow control valve in response to a determination that the user is authorized;
  a manually activated emergency switch configured to allow the user to override the controller to unlock the gas flow control valve when no ID information of an authorized user has been received; and
  an alarm configured to be triggered in response to activation of the emergency switch and to notify facility personnel of the activation of the emergency switch.

19. The lock system according to claim 18, further comprising one or more electronic locks on one or more drawers or cabinet doors, respectively, within an area where the gas flow control valve is located.

20. The lock system according to claim 19, wherein, when the executable instructions are executed by the one or more processors, the one or more processors perform further operations including unlocking the one or more electronic locks on the one or more drawers or cabinet doors, respectively, in response to the determination that the user is authorized.

* * * * *